United States Patent [19]

Okrongly et al.

[11] Patent Number: 5,283,034

[45] Date of Patent: Feb. 1, 1994

[54] STABILIZATION OF STERILIZED SURFACES FOR RESEARCH AND MEDICAL USE

[75] Inventors: David A. Okrongly, Saratoga; Donald Lamons, Mountain View; Thomas B. Okarma, Palo Alto, all of Calif.

[73] Assignee: Applied Immune Sciences, Inc., Santa Clara, Calif.

[21] Appl. No.: 858,125

[22] Filed: Mar. 26, 1992

Related U.S. Application Data

[63] Continuation-in-part of Ser. No. 785,222, Oct. 28, 1991, which is a continuation of Ser. No. 638,030, Jan. 2, 1991, abandoned, which is a continuation of Ser. No. 374,091, Jun. 29, 1989, abandoned.

[51] Int. Cl.$^5$ .............................................. H61L 2/00
[52] U.S. Cl. .................................. 422/22; 422/20; 422/21; 435/181
[58] Field of Search ............... 435/173, 175, 181, 174; 422/20, 21, 22

[56] References Cited

U.S. PATENT DOCUMENTS

| | | | |
|---|---|---|---|
| 1,676,579 | 7/1928 | Schneider et al. | 435/173 |
| 3,016,336 | 1/1962 | Scott et al. | 435/174 |
| 3,645,849 | 2/1972 | Gray | 422/21 |
| 4,250,139 | 2/1981 | Luck et al. | 422/21 |
| 4,438,198 | 3/1984 | Schmer | 435/181 |
| 4,460,445 | 7/1984 | Rekers | 204/159.2 |
| 4,620,908 | 11/1986 | Van Duzer | 422/22 |
| 4,727,027 | 2/1988 | Wiesehahn et al. | 435/173 |
| 4,736,019 | 4/1988 | Bellattar et al. | 435/181 |

OTHER PUBLICATIONS

Woolston, Med. Design & Material (Jan. 1991) 1:42-51.

*Primary Examiner*—Robert J. Warden
*Assistant Examiner*—Krisanne M. Thornton
*Attorney, Agent, or Firm*—Timothy J. Lithgow

[57] ABSTRACT

A method and composition which permits sterilization of surfaces coupled with biologically active moieties by ionizing radiation is described. The protecting composition contains a surface-stabilizing agent which adheres to the surface and has a molecular weight ≧5 kd, and an oxygen radical scavenger which is preferably a di- or polysaccharide or reduced form thereof. In the method of the invention, a surface which is coupled to a biologically active agent is protected with the invention composition, dried to a moisture content of less than 1%, and then sterilized by ionizing radiation under standard conditions. The sterilized surfaces of the invention are particularly useful in the production of medical devices intended for extracorporeal use, particularly in cell-separation techniques.

44 Claims, 4 Drawing Sheets

STABILIZATION OF STERILIZED SURFACES FOR RESEARCH AND MEDICAL USE

The present application is a continuation-in-part of U.S. patent application Ser. No. 07/785,222, filed Oct. 28, 1991, which was a file-wrapper-continuation of U.S. patent application Ser. No. 07/638,030, filed Jan. 2, 1991, abandoned which was a file-wrapper-continuation of U.S. patent application Ser. No. 07/374,091, which was filed Jun. 29, 1989 abandoned. Each of the foregoing applications is incorporated by reference herein.

TECHNICAL FIELD

The invention relates to medical or research devices that contain sensitive reagents and require sterilization. More particularly, the invention concerns means to stabilize the active components contained in such devices in irradiation sterilization procedures.

BACKGROUND ART

There is extensive experience in the immobilization of biologically active molecules to surfaces for research and clinical use. Techniques for enzyme immobilization, adsorption of affinity reagents such as antibodies to surfaces for use in separation procedures and diagnostic assays, and covalent attachment of such reagents or enzymes to surfaces for industrial and medical use are known. More recently, medical devices which incorporate biologically active molecules as functional components have been employed in extracorporeal treatments wherein the treated fluids from the patient will be used directly for administration. It is not practical to treat the fluid which is exiting the device so as to assure freedom from contamination that might have been acquired in transit. Therefore, it is essential that the device through which the fluid is passed itself be sterile.

Ordinary techniques, such as autoclaving and irradiation for sterilizing medical equipment are problematic because these procedures would inactivate the biologically active molecule that is an integral part of the apparatus. Furthermore, the biologically active molecule may be destabilized by the process of coupling it to the surface, and techniques are needed to provide stability with respect to this aspect, as well.

There are many reports of coupling active biological materials to solid support. For example, Larsson, P. H., et al., *J Immunol Meth* (1989) 116:293–298, describe a method for covalent attachment of antibodies to polystyrene dishes wherein the resulting covalently derivatized dishes can then be used in cell depletion procedures in a panning process. U.S. Pat. No. 4,933,410, issued 12 Jun. 1990, also describes a method for derivatizing polystyrene surface so as to acquire the capability covalently to bind active proteins such as antibodies and their fragments, protein A, complexing agents, and other substituents. Derivatization of a polystyrene surface through covalent linkage to antibodies or their fragments is also described by Peterman, J. H., et al., *J Immunol Meth* (1988) 111:271–275; Chu, V. P., et al., *J Ap Polymer Sci* (1987) 34:1917–1924, describes covalent derivatization of polystyrene surfaces for immunoassay protocols. In addition, enzyme immobilization using covalent linkages was described by Rossi, V., et al., *Int J Art Org* (1981) 4:102–107. The immobilization of arginase, described in this article, did not include procedures for sterilization; however, in a subsequent article, Callegaro, L., et al., *Int J Art Org* (1983) 6:19–96, the same group describes the use of fibers containing L-asparaginase which are sterilized using γ-irradiation, under conditions, not specified, which apparently did not completely inactivate the enzyme. None of the other references cited above address the problem of sterilization of the activated surfaces.

The difficulties of using ionizing radiation to sterilize solid surfaces containing biologically active materials was disclosed with respect to Factor XIII grafted onto collagen films by Blanchy, B. G., et al., *J Biomed Mat Res* (1986) 20:469–479, which describes the sensitivity of Factor XIII to γ-radiation. Some improvement was effected by utilizing electron beam irradiation.

The problem of providing sterile activated surfaces is addressed directly by a number of publications. A general summary of approaches to sterilization of medical devices or biosensors is provided by Cesar, E. Y., et al., "Biosensors in Artificial Organs," *ASAIO Trans* (1987) 33:840–845. Some of the literature reviewed in this publication includes a description of the use of antibiotics to sterilize a glucose sensor (Kondo, T. et al., *Diabetes Care* (1982) 5:218:221); the use of propylene oxide to sterilize immunoadsorbents (Sato, H., et al., *Int J Art Org* (1985) 8:109–114), and ionizing radiation is described by Sato, H., et al., *Int J Art Org* (1986) 9:131–136. In the last paper cited, it was noted that losses were observed in adsorptive capacity of the conjugated antibodies even after freeze-drying from a 2% mannitol solution. Woolston, J., in *Med Device Technol* (1990) 1:24–31, gives a general survey of publications on the irradiation sterilization of medical devices which contain biologically active proteins.

Because ionizing radiation is known to effect chemical reactions in the target, the nature of these reactions has been explored with respect to peptides and proteins in a series of articles by Davies, K. J. A., and others in *J Biol Chem* (1987) 20:9895–9901, 9902–9907, 9908–9913. In this series of papers, it is noted that chemical scavengers for oxygen radicals, including t-butyl alcohol, isopropyl alcohol, mannitol, and urate could protect irradiated molecules from chemical degradation due to the products of radiation. This general picture of the chemical effects of irradiation is also described in a review article by Garrison, W. M., *Chem Rev* (1987) 87:381–398.

The construction of a surface with covalently attached monoclonal antibody and sterilized for medical use is described by Morecki, S., et al., *J Biol Resp Modif* (1990) 9:463–474. As is generally the case in providing surfaces with biologically active materials which are supplied in dried form, the surface is blocked with albumin before drying to stabilize the biological material during the drying process and in the dried state. The dried surfaces were reported to be sterilized using electron beam irradiation. No comment is made as to the effect of the irradiation sterilization process on the effectiveness of the resulting surface in adsorbing target cell subsets.

Taken together, the foregoing reports indicate that sterilization of surfaces to which biologically active materials, especially proteins, are coupled, gives unpredictable results with respect to maintaining the activity or binding capacity of the coupled active factors. There is clearly a need for a protocol that can assure the integrity of the biocapacity of the surface when irradiation sterilization is employed to assure freedom from contamination.

DISCLOSURE OF THE INVENTION

The invention provides a method to effect sterilization of a support, usually contained in a device intended for medicine or research, to which surface is coupled at least one biologically active agent. The sterilization procedure utilizes ionizing radiation in the presence of both a surface-stabilizing agent and an oxygen radical scavenger. Typical surface-stabilizing agents are those conventionally used in immunosorbents, such as human serum albumin, ovalbumin, fetuin, collagen, or bovine serum albumin; suitable scavengers include alcohols or polyols such as sucrose or other saccharides.

Thus, in one aspect, the invention is directed to a method to effect sterilization of a hydrophobic polymeric surface to which is coupled at least one biologically active agent, which method comprises subjecting said coupled surface to ionizing radiation of sufficient duration and intensity to substantially free said coupled surface from contamination by virus or microorganisms, wherein said surface has been treated with an amount of a protective composition containing at least one surface-stabilizing agent and at least one oxygen radical scavenger, effective to preserve the activity of the biologically active agent, followed by drying to <1% moisture. The drying is preferably done after the surface has been packaged in a moisture impermeable envelope that is also insulating with respect to infectious agents.

In other aspects, the invention is directed to surfaces coupled to a biologically active molecule which have been sterilized according to the method of the invention, and to methods of using these coupled surfaces in extracorporeal treatment. In still another aspect, the invention is directed to coupled surfaces which have been protected using the protective composition of the invention.

MODES OF CARRYING OUT THE INVENTION

The invention provides a method whereby protective compositions can be used to coat surfaces coupled with at least one biologically active agent. These compositions protect the activity of this agent in a sterilization process using ionizing radiation. The compositions of the invention contain at least one surface stabilizing agent which is a relatively high molecular weight moiety adherent to the coated surface, such as HSA, BSA, collagen or ovalbumin, or is a glycoprotein, such as fetuin or immunoglobulin. The protective composition also contains at least one scavenger for oxygen radicals (formed by interaction of the radiation with water present in the target), which scavenger is preferably a polyol, such as sucrose or other saccharide, or is a glycoprotein. Both the scavenging and stabilizing properties may be provided by a single reagent such as a glycoprotein. Thus, the scavenger for oxygen radicals and the surface-stabilizing agent may be supplied separately or together and may be represented by different components or the same component. Further, mixtures of oxygen radical scavenging agents and/or mixtures of surface-stabilizing agent may also be used. Any combination of materials or a single material having these properties may be used. The surface coupled to a biologically active material to be sterilized is first coated with the composition containing at least these components, dried to <1% moisture content, preferably packaged, and then irradiated with a sufficient amount of ionizing radiation to substantially destroy any microbial or viral contaminants at the surface.

The surface to which the biologically active moiety is coupled is a polymeric surface such as polystyrene, polyethylene and the like. Many articles of manufacture provide such surfaces, including microtiter plates, biosensor substrates, cell culture flasks, cell treatment devices, catheters and other medical tubing, beads, fibers, membranes and the like.

The biologically active agent is generally a protein, and usually an antibody or immunoreactive fragment thereof or an enzyme. However, other biologically reactive moieties may also be used, such as avidin, streptavidin, DNA, RNA, peptides, receptor ligands, glycoproteins, and the like. Any biological material which is "active" by reason of its catalytic and/or binding activity is included in the definition of "biologically active agent."

By "coupled to the surface" is meant that the biologically active agent is associated intimately with the surface during the use of the article in which the surface is contained. The coupling may be passive, i.e., by adsorption, or covalent. Adsorption of antibodies, for example, on microtiter plates for use in immunoassays is well known in the art. Other instances of adsorption of active materials include adsorption of affinity ligands onto surfaces for separations. The biologically active moiety may also be coupled by covalent bonding. The literature cited in the Background section above provides a number of reports of covalent linkage of biologically active moieties to such surfaces. Of particular importance is the disclosure of U.S. Pat. Nos. 4,933,410 and 4,978,724, which describe a high-density derivatization of a polystyrene surface to permit covalent binding of active moieties. This method is that represented by reaction scheme 1 hereinbelow.

The "surface-stabilizing agent" in the invention compositions blocks active sites on the coated surface and protects the coupled active moieties from degradation during, for example, drying processes wherein the surface is depleted of excess moisture. The use of HSA and BSA for this purpose is well known in the art. Any high molecular weight (greater than about 5 kd) material which is adherent to the surface to be employed can be used. Often such agents include collagen and ovalbumin. It is preferred, of course, if the article is a medical device, that the stabilizing agent also be biocompatible and nontoxic. Thus, while, for example, polyethylene glycol might be practical with respect to an article, the products of which are not to be used as medicaments, the use of more conventional stabilizing agents for medical devices is preferred.

The "oxygen radical scavenger" generally is a polyol, preferably a saccharide such as a monosaccharide, disaccharide, or a polysaccharide such as glucose, sucrose, lactose, trehalose, amylose and the like, or a reduced form thereof such as mannitol. As the essential feature of a radical scavenger appears to reside in the presence of hydroxyl groups; mono-, di-, tri-, oligo- and polysaccharides are useful as convenient sources of polyols. Glycoproteins such as fetuin or immunoglobulin are useful both as an oxygen radical scavenger and as a protective agent.

The oxygen radical scavenger and the surface-stabilizing agent can be mixed and applied together to the surface, can be applied separately, can be applied as mixtures of several oxygen radical scavengers, and mixtures of surface-stabilizing agents, or may be applied as a single component having both properties, or as mixtures of components having both properties. For example, the protective composition can be a mixture of HSA and sucrose, or the HSA may be first applied, followed by application of a solution of sucrose, or a mixture of collagen and ovalbumin may be first used to coat the surface, followed by a solution of mannitol, or a solution of the glycoprotein fetuin may be used.

The concentration of the protective agents in the coating solution is not critical, so long as sufficient protective agent is employed adequately to coat the surface to be sterilized. Typically, concentrations of these agents in the range of 0.1% (w/v) to 5% (w/v) are used, although higher concentrations maybe possible, depending on the solubility of the protecting agents. In any event, after each coating step the surface is dried; thus, the initial concentration of the solution becomes unimportant.

Before conduct of the irradiation sterilization step, the surface should be dried to a moisture content of less than 1% (w/v). This drying can be conducted by any suitable means, but it is preferred that this drying be conducted under vacuum so that the evaporation process is accelerated and so that it is not necessary to employ elevated temperatures unnecessarily. It is also preferred to package the dried surface in a water-impermeable envelope, such as, for example, high-density polyethylene, so that the surface does not take up moisture during storage or during the irradiation process. Other packaging materials include foil/polyolefin, foil/polyester, and laminates of polyolefin/nylon/Mylar. Of course, it is advantageous to package the surface prior to irradiation so that the sterile conditions are maintained when the irradiation step has been completed.

For drying, in a typical protocol, the surfaces are either placed directly into a vacuum chamber or frozen prior to placement in a chamber, and the chamber pressure is reduced to $\leq 0.1$ torr for 24 hours. The temperature range for the chamber is $-20°$ to $+25°$ C.

The ionizing radiation is generally either electron beam or $\gamma$-irradiation provided at 0.5-5 Mrad. The general techniques of irradiation sterilization are well known in the art, and the general practice is followed in combination with application of the protective compositions of the invention.

Generally, the protective composition, containing at least one surface stabilizing agent and at least one oxygen radical scavenger, which may be at least one single compound having both these properties, is supplied as a solution, generally an aqueous solution. The solution is applied to the surface to be sterilized and the surface is then incubated for 30 minutes to several hours at room temperature before decanting the solution and drying the surfaces, preferably under vacuum. The concentration of the ingredients of the invention composition is generally on the order of 1-10%, preferably around 2%, for the oxygen radical scavenger and about 0.1-1%, preferably about 0.2% for the surface stabilizing agent or glycoprotein. It is preferred that the active ingredients of the protective composition be applied together, although separate application of the surface stabilizer and the oxygen radical scavenger is also within the scope of the invention. The resultant coated surface will, in all instances, contain both. Thus, in general, the required components of the protective composition are applied either individually or together to the coupled surface to be sterilized; the protected surface is then dried to <1% moisture content, packaged, and then subjected to irradiation using an electron beam or gamma radiation source under standard sterilization conditions at an intensity and for a time duration sufficient to decontaminate the surface of any viral or microbial contaminants, and the surface is then maintained in sterile surroundings until use.

The prepared surface is then conveniently used for any suitable purpose, typically extracorporeal treatment of biological fluids. Such treatment may be effected with respect to treating the body fluids of a single patient wherein the fluid is returned to the same individual after treatment, or the surface may be used to prepare biological fluids for administration to patients in general. One particularly useful extracorporeal treatment involves the depletion of biological fluids derived from individuals of certain cell populations and either recovering the cells adsorbed to the surface as the useful biological product or, conversely, depleting the fluid of unwanted cell populations. The applications of the sterilized biologically-activated surfaces of the invention are numerous and involve a variety of medical and diagnostic techniques.

The following examples are intended to illustrate but not limit the invention.

Preparation A

Activation of Polystyrene Surfaces

In the examples below, surfaces for adsorbent or covalent coupling to the biologically active moiety are prepared using 96-well Immulon-1 plates or tissue culture flasks. The chemistry for the covalent coupling procedure is shown in reaction scheme 1.

To prepare the surfaces for covalent derivatization, a 0.2M solution of N-(hydroxymethyl)-2-bromoacetimide in sulfolane was combined 1:1 (v:v) with a 2M trifluoromethane sulfonic acid solution in sulfolane and swirled gently. The solution was immediately placed in contact with the polystyrene by adding 200 µl to each well of the plates or adding 5 ml to a 25 cm² screw-top tissue culture flask. The plates were covered with adhesive-backed mylar tape and swirled on a platform rotator at 100 rpm; the flasks, after capping tightly, were placed culture-surface down and swirled gently on a platform rotator at 70 rpm. After 2 hours in each case, the solution was decanted and the surface washed with water 10x followed by air-drying at room temperature overnight. All activated surfaces were stable for at least six months under ambient conditions.

EXAMPLE 1

Goat Antimouse IgG 96-Well Plates

The derivatized 96-well plates were coated with 100 µl/well of goat antimouse IgG (GAM, Jackson Immunoresearch, West Grove, Pa.) in Dulbecco's phosphate-buffered saline (DPBS) for 2 hours at room temperature at concentrations of 40, 20, 10, 5, 2.5, 0.625 and 0 µg/ml, each in sextuplicate. After coating, the plates were washed 5x with wash buffer (DPBS containing 0.02% w/v BSA and 0.05% v/v Tween-20).

Those plates to be stabilized with the invention composition were treated with 200 µl/well 0.2% HSA/2% sucrose in DPBS for 30 min at room temperature followed by removing the excess protective composition by aspiration.

The plates were then placed in a vacuum chamber at 0.1 torr for 72 hours between −20° and +25° C. and packaged at less than 5% RH.

Those plates that were sterilized were irradiated with 2.5–2.9 Mrad of electron beam radiation.

All plates were prepared for testing by rinsing with DPBS and incubating for 1.5 hours at room temperature with 200 µl/well blocking solution (0.1M sodium carbonate, pH 9.5, containing 0.1% BSA) followed by rinsing with wash buffer.

The wells were tested in quadruplicate by incubating with 100 µl/well with 0.10 µg/ml horseradish peroxidase (HRP)-conjugated mouse IgG in wash buffer for 1.5 hours at room temperature. Simultaneously, duplicate wells at each coating concentration were tested for specific inhibition by incubation with the HRP-mIgG solution containing 1.0 µg/ml mouse IgG.

All wells were rinsed with wash buffer and incubated with 100 µg/well of substrate ABTS. The reaction in the wells was terminated with ABTS stop solution when the OD at 405 nm was greater than 1 for any set of wells. At all coating concentrations and under all plate preparation conditions, specific inhibition was achieved with mIgG (OD 405 nm less than or equal to 0.015).

Figure 1:
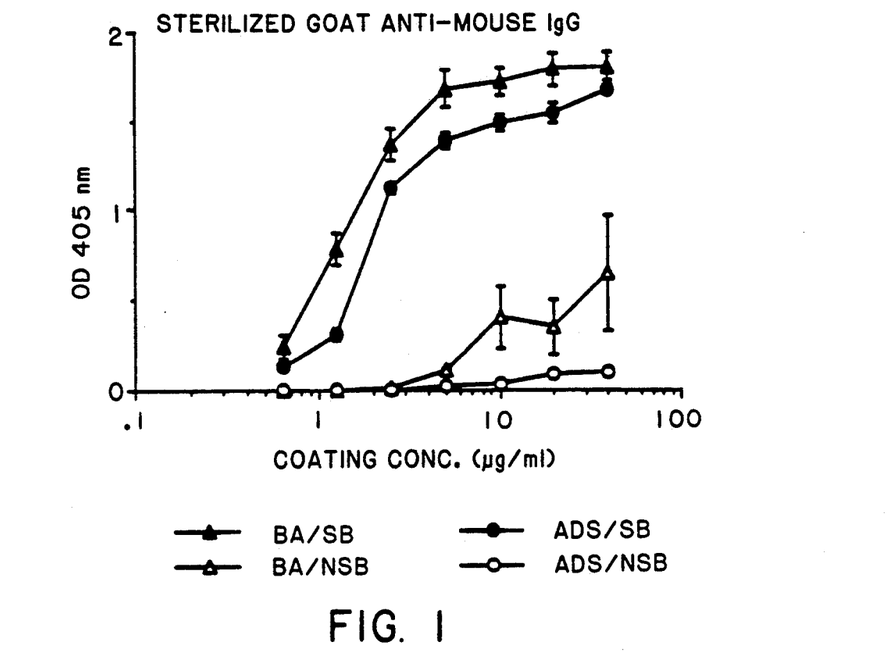
FIG. 1 compares the ability of goat antimouse IgG coupled by adsorption or covalent bonding to a polystyrene surface to capture labeled mouse IgG after irradiation sterilization with and without the protective composition of the invention.

The stabilizing effect of the sucrose/HSA composition is shown in FIG. 1. In FIG. 1, only sterilized plates were tested. The figure shows binding after irradiation sterilization of mouse IgG-HRP conjugate to goat antimouse IgG immobilized on bromoacetamide-derivatized polystyrene (BA) or adsorbed noncovalently to polystyrene (ADS), and tested either with (SB) or without (NSB) 0.2% HSA/2% sucrose stabilizer used prior to irradiation sterilization. The HRP substrate ABTS was used to detect the presence of the bound conjugate. Error bars represent one standard deviation of quadruplicate determinations. The triangles represent plates having covalently bound goat antimouse IgG; the circles represent plates to which the goat antimouse IgG was adsorbed using standard adsorption application techniques. The closed triangles and circles represent plates where sterilization was conducted after application of the protective composition; the open triangles and circles represent plates where no protective composition was applied. As FIG. 1 shows, the capture capacity of the antibody-coupled plate increases with concentration of the coupled antibody as expected when sterilization was conducted on plates which had been protected with the HSA/sucrose composition. However, very little capture activity was shown where sterilization was conducted absent the protective composition.

Figure 2:
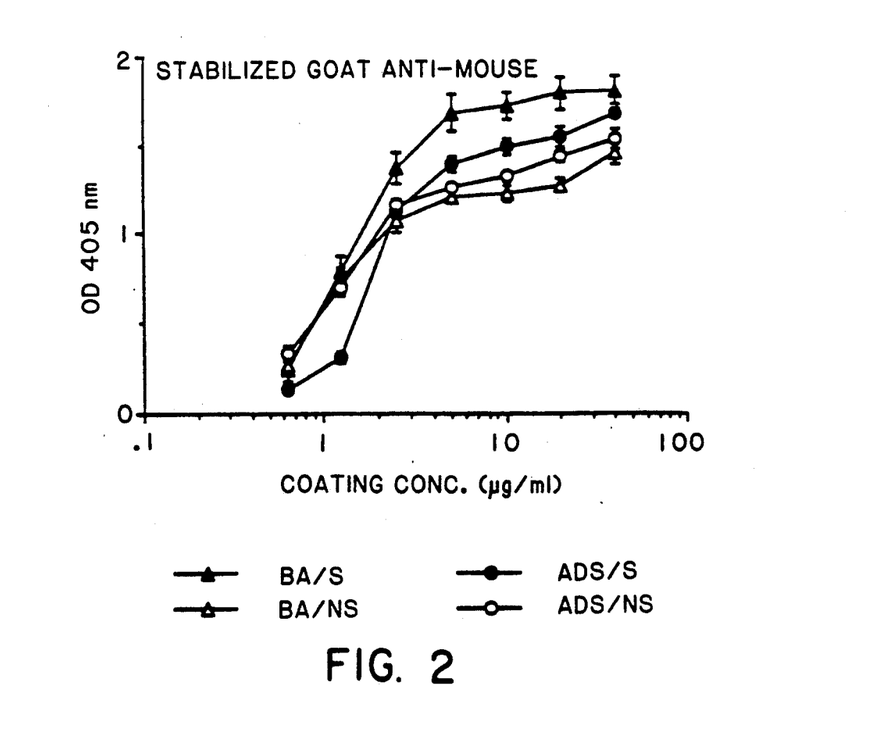
FIG. 2 shows the results of a control wherein goat antimouse IgG coupled to polystyrene surfaces is stabilized with the protective composition and either sterilized or not sterilized with ionizing radiation.

FIG. 2 represents the results of a control experiment wherein all of the plates tested had been treated with the protective composition. This figure shows binding of mouse IgG-HRP conjugate to immobilized goat antimouse IgG stabilized with HSA/sucrose on bromoacetamide-derivatized polystyrene (BA) or adsorbed noncovalently to polystyrene (ADS). Activity or nonsterile (NS) and sterile (S) plates were compared, using ABTS to detect the presence of the bound conjugate. Error bars represent one standard deviation of quadruplicate determinations. Similar and expected activity patterns were observed as a function of concentration, whether or not the plates were sterilized, and whether or not the antibody had been adsorbed or covalently bound.

EXAMPLE 2

Streptavidin 96-Well Plates

Streptavidin-coated plates were prepared as described in Example 1, except that streptavidin was substituted for goat antimouse IgG. The plates were washed, stabilized with the protective composition (in some cases), vacuum-dried, irradiated (when applicable), rinsed and blocked as described in Example 1.

The plates were then tested by incubation with 100 μl/well of 0.10 μg/ml of biotinylated HRP in wash buffer for 1.5 hours at room temperature; specific inhibition was verified by incubation with biotinylated HRP solution containing 1 μg/ml biotin. The plates were washed with wash buffer and the wells incubated with 100 μl/well of ABTS and the reaction conducted and read as described above.

Figure 3:
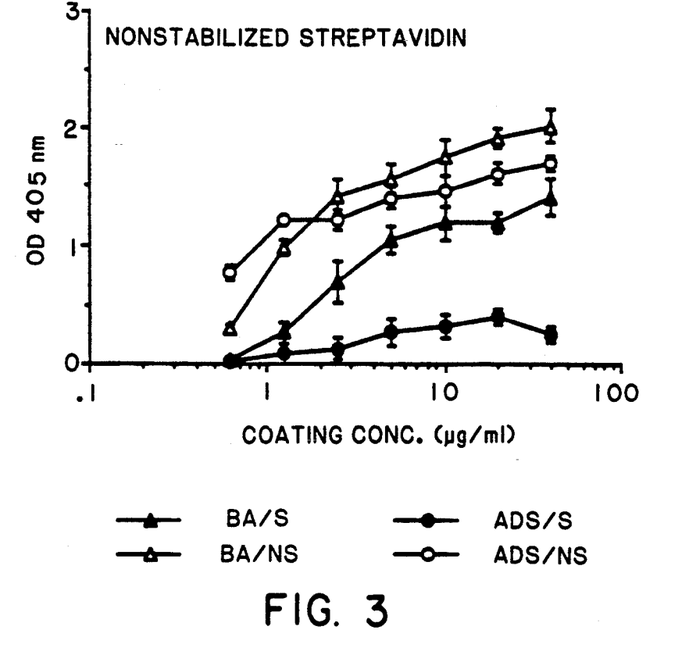
FIG. 3 is a graph which compares the ability of streptavidin immobilized covalently or noncovalently to polystyrene surfaces to bind biotinylated HRP on sterile and nonsterile plates without treatment with the protective composition.

The results are shown in FIG. 3 for plates that had not been protected with the protective composition of the invention. Thus, FIG. 3 shows binding of biotinylated HRP to streptavidin immobilized without stabilization on bromoacetamide-derivatized polystyrene (BA) or adsorbed noncovalently to polystyrene (ADS). Binding activity of the conjugate was compared on nonsterile (NS) and sterile (S) plates, with ABTS used to detect the bound conjugate. Error bars represent one standard deviation of quadruplicate determinations. The results show that sterilization of these unprotected plates inactivates the streptavidin, especially in the case of plates prepared by adsorption of the streptavidin (solid circles). The unsterilized plates, shown by open triangles and circles, show the expected activity curves; some diminution in the activity curve is shown for the covalently coupled sterilized plates (closed triangles).

EXAMPLE 3

Horseradish Peroxidase 96-Well Plates

The plates were prepared, treated with protecting composition (if applicable), sterilized (if applicable), and tested for activity as described in Examples 1 and 2 above, except for substituting HRP at 160, 80, 40, 20, 10, 5, 2.5 and 0 μg/ml for goat IgG or streptavidin as the initially coated biologically active- moiety. The results of these determinations are shown in FIGS. 4 and 5.

Figure 4:
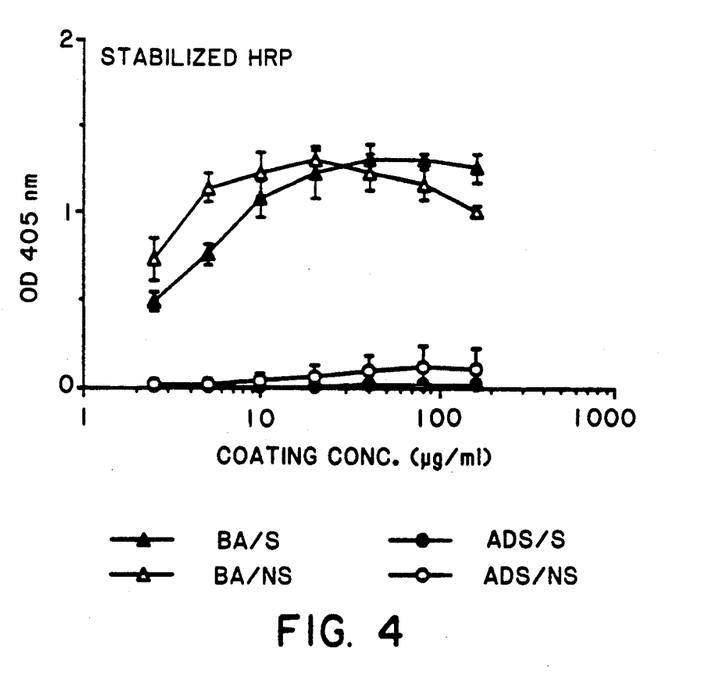
FIG. 4 is a graph comparing the activity of HRP coupled covalently or noncovalently to polystyrene and treated with the protective composition on plates that were and were not treated with ionizing radiation.

FIG. 4 shows activity of HRP stabilized with HSA/sucrose following immobilization on bromoacetamide-derivatized polystyrene (BA) or adsorbed noncovalently to polystyrene (ADS). HRP activity was compared for both nonsterile (NS) and sterile (S) plates. ABTS was used to detect the presence of active HRP. Error bars represent one standard deviation of sextuplicate determinations. FIG. 4 shows the results for plates all of which had been stabilized with the protective composition of the invention. These results show that adsorption of HRP to the polystyrene plates does not produce an active product, whether or not the plate is sterilized (closed and open circles, respectively). However, both sterilized and unsterilized plates to which HRP was covalently bound show expected activity curves as a function of concentration.

Figure 5:
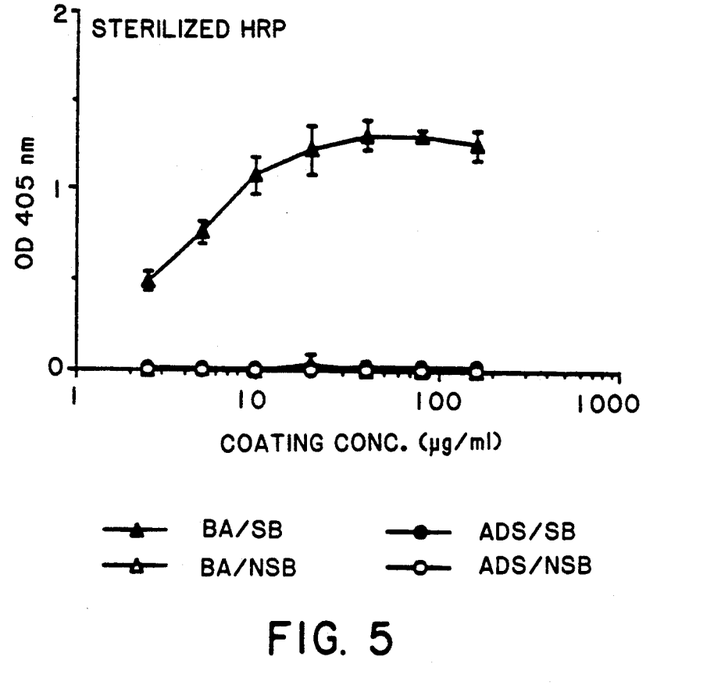
FIG. 5 shows the activity of HRP coupled covalently or noncovalently to polystyrene sterilized with and without the protective composition of the invention.

FIG. 5 shows activity after irradiation sterilization of HRP immobilized on bromoacetamide-derivatized polystyrene (BA) or adsorbed noncovalently to polystyrene (ADS), and tested either with (SB) or without (NSB) HSA/sucrose stabilization. ABTS was used to detect the presence of active HRP. Error bars represent one standard deviation of sextuplicate determinations.

FIG. 5 shows that the presence of the protective composition is needed to maintain the activity of HRP. As before, the plates to which the HRP was simply adsorbed show little or no activity; sterilized plates, where sterilization was conducted in the absence of the protective composition (open triangles), also show no activity. Only the stabilized covalently bound HRP-coated plates survive sterilization by irradiation.

EXAMPLE 4

Anti-CD8 mAb Tissue-Culture Flasks

Bromoacetimide-derivatized tissue-culture flasks, prepared as in Preparation A, were treated with 5 ml of 50 μg/ml solution of anti-CD8 mAb (AIS, Menlo Park, Calif.) for 2 hours at room temperature on a platform shaker at 50 rpm. The mAb solution was decanted and the flasks were immediately washed 10× with DPBS and coated for 30 minutes at room temperature with either 5 ml 0.2% HSA/2% sucrose in DPBS; or 5 ml 0.2% HSA in DPBS; or 5 ml 2% sucrose in DPBS. The coating solutions were decanted and the flasks vacuum-dried at 0.1 torr for 72 hours at −20° to +25° C. The flasks were packaged under nitrogen in a moisture-barrier bag at less than 5% relative humidity. All but one of the flasks were then sterilized using either electron beam radiation or γ-radiation at 2.5–2.9 Mrad.

The capacity of the treated flasks to separate $CD^{8}+$ human lymphocytes from PBMC was then tested. About $6 \times 10^7$ fresh PBMC were incubated at room temperature with 0.5% heat-inactivated human γ-globulin and introduced into the anti-CD8 mAb-coated tissue culture flasks. After 1 hour incubation at room temperature, the nonadherent cells were removed with DPBS and analyzed by flow cytometry. The adherent cells were cultured for 72 hours at 37° C., 5% $CO_2$ with 5 ml culture medium containing RPMI 1640; 0.1 μg/ml phytohemagglutinin; 300 IU/ml recombinant human IL-2; 50 μg/ml gentamycin; and 10% fetal calf serum. After the culture period, most cells were in suspension; the majority of the remaining adherent cells were released by gentle pipetting from the surface with the culture media. The cells were pooled, placed in standard tissue culture flasks for further growth in the same medium with the cell concentration adjusted to $0.5 \times 10^6$ cell/ml, and fresh medium as added as needed. Viability was determined by Typan Blue exclusion, and purity was determined by flow cytometric staining with the appropriate staining reagents.

Figure 6:
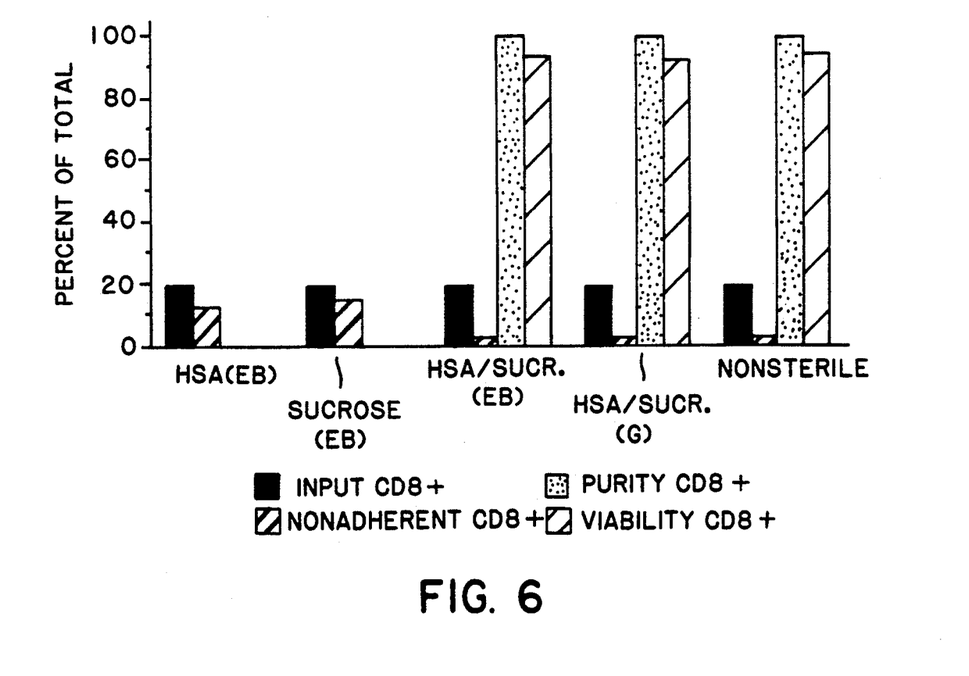
FIG. 6 shows the ability of anti-CD8 monoclonal antibody covalently immobilized to polystyrene in tissue culture flasks to capture CD8+ cells after sterilization in the presence of HSA alone, sucrose alone, or the combination of HSA and sucrose using either electron beam radiation or γ-radiation, and in comparison with unsterilized plates.

The results for the various flasks are shown in FIG. 6, which thus depicts comparison of $CD8+$ PBMC binding, purity, and viability for tissue culture flasks containing covalently immobilized anti-CD8 monoclonal antibody. Flasks were coated with 50 μg/ml anti-CD8 and treated as follows: stabilized with 0.2%, HSA and electron beam-sterilized [HSA (EB)], stabilized with 2.0% sucrose and electron beam-sterilized [sucrose (EB)I, stabilized with HSA/sucrose and electron beam-sterilized [HSA/sucrose (EB)], stabilized with HSA/sucrose and gamma-sterilized [HSA/sucrose (G)], and HSA/sucrose-stabilized and no irradiation sterilization [nonsterile]. All values are the average of triplicate determinations. Purity and viability were determined after seven days in culture, except for HSA and sucrose flasks, due to insufficient cell capture.

As shown in FIG. 6, nonsterilized flasks showed a high capacity to effect adherence of $CD8+$ cells. The count of nonadherent CD8+ cells is much less than the input level CD8+ cells. The adhered cells were almost 100% CD8+ and viable.

Similar results to those observed in nonsterile flasks were obtained when the sterilized flasks were pretreated with the protective composition, whether sterilization was conducted using electron beam or γ-irradiation. However, in those flasks where only HSA or sucrose was used to pretreat the flask surface before sterilization, so few CD8+ cells adhered to the surface that purity and viability could not be tested.

EXAMPLE 5

Figure 7:
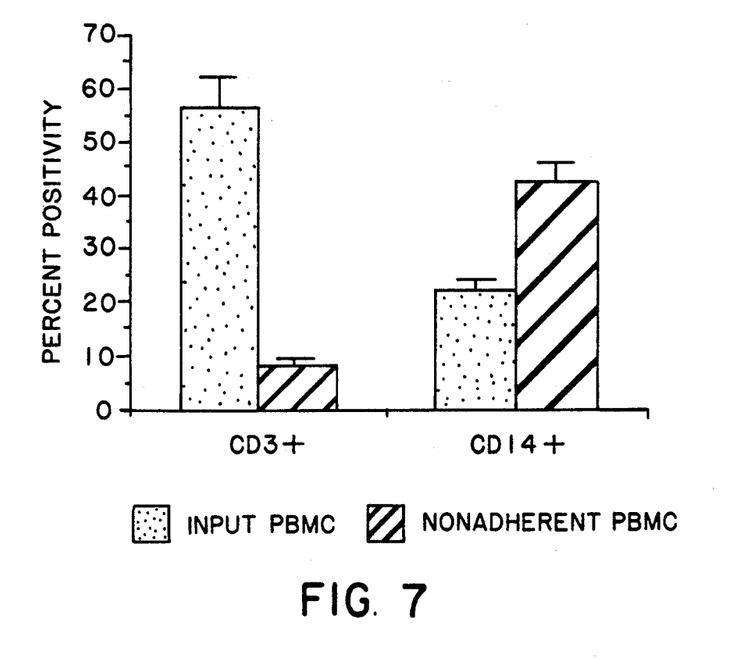
FIG. 7 shows the ability of anti-CD3 monoclonal antibody covalently immobilized to polystyrene to capture CD3+ cells to the exclusion of CD14+ cells. The surface was sterilized using ionizing radiation after drying in the presence of HSA and sucrose.

To further demonstrate the specificity of the cell selection process in sterile tissue culture devices, anti-CD3 mAb was covalently immobilized to bromoacetamide flasks and irradiation-sterilized with electron beam, as described in Example 1. A $2 \times 10^7$ PBMC cell load was added to each device, and after the standard 1-hour incubation period, the nonadherent cells were removed and analyzed by flow cytometry. The data from a total of nine experiments are shown in FIG. 7. FIG. 7 shows depletion of CD3+ T cells from PBMC, with corresponding enrichment of CD14+ monocytes, by electron beam-irradiated anti-CD3 cell separation device. Average of nine separations shows 90% depletion of CD3+ cells and 98% enrichment of CD14+ cells.

On average, 90% of the CD3+ cells were depleted during the cell separation process. This efficient removal of the CD3 subset was accompanied by a 92% enrichment of CD14+ monocytes. Monocyte enrichment is a particularly good indicator of specificity due to the strong tendency for the monocytes to nonspecifically adhere to plastic, in particular polystyrene (30). This demonstrates the effectiveness of the cell separation devices to remove only the target cell subpopulations without significantly affecting nontargeted phenotypes.

We claim:

1. A method for preparing a polymeric surface, which method comprises:
   providing a polymeric surface which comprises a biologically active agent coupled thereto,
   applying to said surface a protective composition containing at least one surface-stabilizing agent and at least one oxygen radical scavenger, whereby the activity of the biologically active agent is preserved upon subjecting said surface to sterilizing amounts of ionizing radiation; and,
   drying the surface to a moisture content of less than 1%.

2. A polymeric surface comprising a biologically active agent coupled thereto, said polymeric surface prepared according to a method comprising steps of:
   applying to a polymeric surface comprising a biologically active agent coupled thereto at least one surface-stabilizing agent and at least one oxygen radical scavenger, whereby the activity of the biologically active agent is preserved when subjected to sterilizing amounts of irradiation; and then,
   drying said surface to a moisture content of less than 1%.

3. A method for protecting a hydrophobic polymeric surface from degradation when subjected to ionizing radiation, wherein said surface comprises a biologically active agent coupled thereto, which method comprises:
   applying to said surface an amount of a protective composition containing at least one surface stabilizing agent and at least one oxygen radical scavenger effective to preserve the activity of the biologically active agent when subjected to sterilizing amounts of irradiation.

4. The method of claim 3, further comprising a step of drying said surface.

5. The method of claim 1, further comprising a step of subjecting said surface to sterilizing amounts of ionizing radiation.

6. The surface prepared according to claim 2, wherein the preparation further comprises a step of subjecting said surface to sterilizing amounts of ionizing radiation.

7. The method of claim 1 wherein said drying is conducted under vacuum.

8. The method of claim 5 wherein the surface is packaged after drying and before said subjecting to radiation.

9. The method of claim 1, wherein the biologically active agent is an antibody or an immunologically reactive fragment thereof.

10. The method of claim 1 wherein the biologically active agent is avidin or streptavidin.

11. The method of claim 1 wherein the biologically active agent is an enzyme.

12. The method of claim 1 wherein the polymeric surface is polystyrene.

13. The method of claim 1 wherein the polymer surface is contained in an apparatus used for extracorporeal treatment.

14. The method of claim 1 wherein the polymeric surface is coupled with a biologically active agent capable of selective cell capture.

15. The method of claim 1 wherein the surface-stabilizing agent is a peptide, protein or glycoprotein of greater than 5 kd MW.

16. The method of claim 1 wherein the surface-stabilizing agent is HSA, BSA, ovalbumin or collagen, or is a glycoprotein.

17. The method of claim 1 wherein the oxygen radical scavenger is a saccharide of at least 2 saccharide units or a reduced form thereof, or is a glycoprotein.

18. The method of claim 1 wherein the oxygen radical scavenger is a mono-, di-, tri-, oligo- or polysaccharide.

19. The method of claim 18 wherein the oxygen radical scavenger is sucrose.

20. The surface of claim 2 wherein the biologically active agent is an antibody or an immunologically reactive fragment thereof.

21. The surface of claim 2 wherein the biologically active agent is avidin or streptavidin.

22. The surface of claim 2 wherein the biologically active agent is an enzyme.

23. The surface of claim 2 wherein the polymeric surface is polystyrene.

24. The surface of claim 2 wherein the polymer surface is contained in an apparatus used for extracorporeal treatment.

25. The surface of claim 2 wherein the polymeric surface is coupled with a biologically active agent capable of selective cell capture.

26. The surface of claim 2 wherein the surface-stabilizing agent is a peptide, protein or glycoprotein of greater than 5 kd MW.

27. The surface of claim 2 wherein the surface-stabilizing agent is HSA, BSA, albumin or collagen, or a glycoprotein.

28. The surface of claim 2 wherein the oxygen radical scavenger is a saccharide of at least one saccharide unit, or a reduced form of saccharides of at least two saccharide units, or is a glycoprotein.

29. The surface of claim 2 wherein the oxygen radical scavenger is a mono-, di-, tri-, oligo- or polysaccharide.

30. The surface of claim 29 wherein the oxygen radical scavenger is sucrose.

31. A method to conduct extracorporeal treatment of body fluid from a patient, which method comprises passing said fluid over a surface coupled to a biologically active agent sterilized and prepared by the method of claim 6 and returning said fluid to the patient.

32. A method to prepare a biological fluid for administration to a patient which method comprises passing said fluid over a surface coupled to a biologically active agent sterilized and prepared by the method of claim 6 and administering said fluid to the patient.

33. The method of claim 4 wherein said drying is conducted under vacuum.

34. The method of claim 4 wherein the surface is packaged after said drying step and before said surface is subjected to radiation.

35. The method of claim 3 wherein said protective composition is applied to said surface by applying said surface stabilizing agent and said oxygen radical scavenger simultaneously.

36. The method of claim 3 wherein said protective composition is applied to said surface by applying said surface stabilizing agent and said oxygen radical scavenger separately to said surface.

37. A surface coupled to a biologically active agent which is protected by the method of claim 3.

38. A method to prepare a sterile polymeric surface comprising a biologically active agent coupled thereto, which method comprises:
    a) applying to a surface comprising a biologically active agent coupled thereto at least one surface-stabilizing agent and at least one oxygen radical scavenger, whereby the activity of the biologically active agent is preserved when subjected to sterilizing amounts of irradiation;
    b) drying said coupled surface to a moisture content of less than 1%; and
    c) subjecting said coupled surface to sterilizing amounts of ionizing radiation.

39. The method of claim 38 which further comprises, prior to step c), packaging said surface in a material which is essentially impermeable to water and microbial or viral agents.

40. The method of claim 38 wherein said surface-stabilizing agent is HSA, BSA, ovalbumin, or collagen, or is a glycoprotein.

41. The method of claim 38 wherein said oxygen radical scavenger is a saccharide of at least one saccharide unit, or a reduced form of saccharides of at least two saccharide units, or is a glycoprotein.

42. The method of claim 40 wherein said glycoprotein is fetuin or immunoglobulin.

43. The method of claim 41 wherein said glycoprotein is fetuin or immunoglobulin.

44. The method of claim 41 wherein said drying is conducted under vacuum.

* * * * *